United States Patent [19]

Rosario-Jansen et al.

[11] Patent Number: 4,954,635

[45] Date of Patent: Sep. 4, 1990

[54] PROCESS FOR PREPARING QUATERNIZED IMIDAZOLINE FABRIC CONDITIONING COMPOUNDS

[75] Inventors: Theresa Rosario-Jansen, Fairfield, Ohio; Glen D. Lichtenwalter, Corsicana, Tex.

[73] Assignee: The Procter & Gamble Company, Cincinnati, Ohio

[21] Appl. No.: 403,541

[22] Filed: Sep. 6, 1989

[51] Int. Cl.$^5$ ................ C07D 239/06; C07D 233/14; C07D 243/04

[52] U.S. Cl. .................... 548/354; 548/352; 544/335; 540/553

[58] Field of Search .............. 548/354, 352; 544/335; 540/553

[56] References Cited

U.S. PATENT DOCUMENTS

| | | | |
|---|---|---|---|
| 2,267,965 | 12/1941 | Wilson | 260/309.6 |
| 2,874,074 | 2/1959 | Johnson | 117/139.5 |
| 3,095,373 | 6/1963 | Blomfield | 252/8.8 |
| 3,681,241 | 8/1972 | Rudy | 252/8.75 |
| 4,127,489 | 11/1978 | Pracht et al. | 252/8.8 |
| 4,233,451 | 11/1980 | Pracht et al. | 548/354 |
| 4,238,373 | 12/1980 | Hardy et al. | 252/542 |
| 4,267,350 | 5/1981 | Tomalia et al. | 548/354 |
| 4,339,391 | 7/1982 | Hoffmann et al. | 260/401 |
| 4,529,803 | 7/1985 | Tomalia et al. | 548/354 |
| 4,654,152 | 3/1987 | Cukier et al. | 252/8.8 |
| 4,724,089 | 2/1988 | Konig et al. | 252/8.8 |

FOREIGN PATENT DOCUMENTS

| | | |
|---|---|---|
| 0248365 | 12/1987 | European Pat. Off. . |
| 2243806 | 4/1974 | Fed. Rep. of Germany . |
| 2430140 | 2/1976 | Fed. Rep. of Germany . |
| J6 1207-669-A | 9/1986 | Japan . |
| J6-12070670-A | 9/1986 | Japan . |
| 980003 | 1/1965 | United Kingdom . |
| 1565808 | 4/1980 | United Kingdom . |

OTHER PUBLICATIONS

R. Puchta, "Cationic Surfactants in Laundry Detergents and Laundry Aftertreatment Aids", J. Am. Oil Chemist' Soc., vol. 61, No. 2, pp. 367–376 (Feb. 1984).

R. R. Egan, "Cationic Surface Active Agents as Fabric Softeners", J. Am. Oil Chemist' Soc., vol. 55, pp. 118–121 (Jan. 1978).

J. March, "Advanced Organic Chemistry: Reactions, Mechanisms, and Structure", pp. 322–323, 1968.

*Primary Examiner*—John M. Ford
*Attorney, Agent, or Firm*—Lars S. Johnson; Leonard W. Lewis; Jerry J. Yetter

[57] ABSTRACT

Disclosed is a high yield process for quaternizing imidazoline ester compounds in the absence of lower alcohol solvents and under anhydrous conditions. The reaction product of this process contains a quaternized imidazoline ester fabric softening compound and, optionally, an imidazoline ester compound. In the process of this invention, an imidazoline ester compound is intitially heated to form an anhydrous melt. This anhydrous melt is subsequently contacted with a quaternizing agent selected from small chain organic halides and sulfates. The imidazoline ester compound and quaterinzing agent are then reacted under anhydrous conditions for a period of time sufficient for substantially all of said quaterinzing agent to react with said imidazoline ester compound to form a quaternized imidazoline ester compound.

17 Claims, No Drawings

PROCESS FOR PREPARING QUATERNIZED IMIDAZOLINE FABRIC CONDITIONING COMPOUNDS

TECHNICAL FIELD

The present invention relates to a process for quaternizing an imidazoline ester compound. The present invention further relates to a process for preparing a composition comprising a quaternized imidazoline ester fabric softening compound and, optionally, an imidazoline ester compound. In particular, the present invention relates to an improved process for quaternizing an imidazoline ester compound in which the quaternization is carried out under anhydrous conditions and in the absence of lower alcohol solvents.

BACKGROUND OF THE INVENTION

Processes for quaternizing amines and imidazoline compounds are known in the art. U.S. Pat. No. 4,529,803, July 16, 1985, Tomalia et al., and U.S. Pat. No. 4,267,350, May 12, 1981, Tomalia et al., disclose a process for preparing an imidazolinium amide salt by (1) reacting an imidazoline with an $\alpha,\beta$-unsaturated ester of a carboxylic acid; (2) reacting the resulting ester imidazoline with a primary or secondary amine; and (3) quaternizing the resulting amide imidazoline product by reacting it with an alkylating agent.

U.S. Pat. No. 4,238,373, Dec. 9, 1980, to Hardy et al., discloses a process for quaternizing tertiary amines in an organic reaction medium comprising a water-soluble or water-dispersible organic compound having a molecular weight greater than 240. The quaternization reaction is carried out by first mixing a tertiary amine containing one or more long chain hydrocarbon residues with the organic reaction medium. This mixture is agitated and the quaternizing agent is then introduced into the mixture in an amount in excess of that stoichiometrically required. The quaternization reaction of this reference may proceed under both anhydrous and aqueous conditions.

U.S. Pat. No. 4,339,391, July 13, 1982, Hoffmann et al., discloses quaternary ammonium compounds, which may optionally contain ester-interrupted alkyl substituents, and methods for their preparation and use. In the disclosed preparation method, an aminoalkylate is reacted with a free fatty acid, without solvents, to form an intermediate amine. The intermediate amine is then dispersed in water and is quaternized with a quaternizing agent. The quaternization may be carried out either in the presence of a lower alcohol solvent or in the absence of such solvent.

German OLS 2430140, published Feb. 19, 1976, assigned to Rewo Chemische Fabrik GmbH, discloses diester quaternary ammonium compounds and several methods for their preparation, including a quaternization method which does not require using a solvent during the quaternization reaction.

British Patent Specification 980,003, Jan. 13, 1965, assigned to L'Oreal, discloses a method of preparing a quaternary ammonium compound wherein quaternization is accomplished by adding a stoichiometric quantity of dimethylsulfate to an amino ester solution containing, among other ingredients, isopropyl alcohol and an amino ester.

Many different types of fabric conditioning agents have been used in rinse-cycle fabric treatment compositions. One class of compounds frequently used as the active component for such compositions includes substantially water-insoluble quaternary nitrogenous compounds having two long chain alkyl groups. Typical of such materials are ditallow dimethyl ammonium chloride and imidazolinium compounds substituted with two long chain alkyl groups. These materials are normally prepared in the form of a dispersion in water.

The use of substituted imidazoline compounds as fabric conditioning agents is known. Imidazoline compounds have been used by themselves or in combination with other agents in the treatment of fabrics. British Patent Specification 1,565,808, issued Apr. 23, 1980, and assigned to Hoechst Aktiengesellschaft, discloses a textile fabric softener composition consisting of an aqueous solution or dispersion of an imidazoline or salt thereof, or a mixture of such imidazolines or salts thereof. U.S. Pat. No. 4,724,089, Feb. 9, 1988, to Konig et al., discloses fabric treatment compositions containing dialkyl imidazoline compounds, or salts thereof, which may have one alkyl chain interrupted by an ester linkage.

The use of imidazolinium salts as fabric conditioning agents is also known. U.S. Pat. No. 2,874,074, Feb. 17, 1959, to Johnson discloses using imidazolinium salts to condition fabrics. U.S. Pat. No. 3,681,241, Aug. 1, 1972, to Rudy, discloses fabric conditioning compositions containing a mixture of imidazolinium salts and other fabric conditioning agents.

It is generally known that when quaternizing imidazoline amide compounds, the imidazoline compound must be in a state wherein it can react with the quaternizing agent. Such a reactive state may be achieved by liquifying the imidazoline through melting or by dispersing or dissolving the imidazoline in a solvent. Lower alkyl (i.e., $C_1$-$C_4$) alcohol solvents are typically used for this. However, when quaternizing an imidazoline ester compound, the presence of such lower alcohol solvents can cause transesterification reactions between the imidazoline ester compound and the lower alcohol solvent.

Additionally, the presence of water during quaternization of an imidazoline ester compound can cause hydrolysis of the imidazoline ester reactant prior to quaternization.

It is therefore an object of the present invention to provide a process for quaternizing an imidazoline ester compound in the absence of lower alcohol solvents and water.

It is another object of this invention to provide a high yield process for preparing a reaction product containing a quaternized imidazoline ester compound and, optionally, an imidazoline ester compound.

It is another object of this invention to provide a process for preparing said reaction product containing a quaternized imidazoline ester compound and, optionally, an imidazoline ester compound at optimum relative concentrations without the need for additional processing.

These objects are realized by the present invention.

SUMMARY OF THE INVENTION

The present invention is directed to a process for quaternizing imidazoline ester compounds, said process comprising:
(a) forming an anhydrous melt of an imidazoline ester compound of the formula

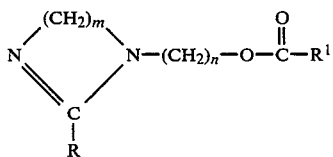

wherein R and R[1] are, independently, a $C_{11}$–$C_{21}$ hydrocarbyl group, and m and n are, independently, from 2 to 4 inclusive;

(b) contacting said anhydrous melt with a quaternizing agent of the formula $R^2X$ or $R^2_2X$, wherein $R^2$ is a $C_1$–$C_3$ alkyl or benzyl group and X is a halide or sulfate, to form a liquid reaction mixture, said liquid reaction mixture being maintained free of lower alcohol solvents; and (c) maintaining said liquid reaction mixture under anhydrous conditions at a temperature ranging from about 50° C. to about 100° C. for a period of time sufficient for substantially all of said quaternizing agent to react with said imidazoline ester compound to form a quaternized imidazoline ester compound of the formula

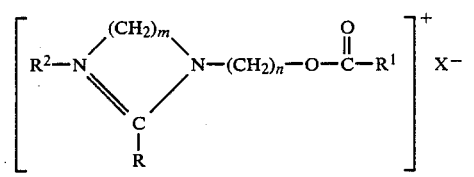

or

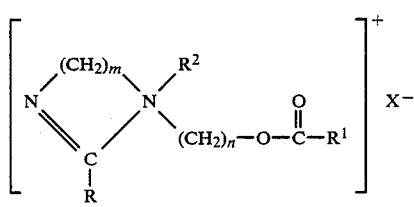

or mixtures thereof, wherein R, R[1], R[2], X, m and n are as hereinbefore defined.

DETAILED DESCRIPTION OF THE INVENTION

In accordance with this invention, a process for quaternizing an imidazoline ester compound is described herein. The reaction product of said process contains from about 1 to 100 mole percent, preferably from about 30 to about 90 mole percent, most preferably from about 40 to about 80 mole percent, of quaternized imidazoline ester compounds and from 0 to about 99 mole percent, preferably from about 70 to about 10 mole percent, most preferably from about 60 to about 20 mole percent, of the initial imidazoline ester reactant. The process disclosed herein results in a higher conversion of imidazoline ester compound to the desired quaternized imidazoline ester compound with minimal side reactions. The process also results in a reaction product substantially free of quaternizing agent.

A further advantage of the process is that the reaction product which results can be used for preparation of stable, liquid fabric and fiber (including hair) treatment compositions without substantial further processing, such as purification, solvent stripping, and blending of imidazoline ester and quaternized imidazoline ester compounds. The reaction product can also be solidified and used for fabric treatment by releasably affixing it to a solid carrier. When used in fabric treatment applications, said reaction product may be used in formulations containing both detergents and fabric softener actives, as well as in formulations containing only fabric softener actives.

The process for quaternizing an imidazoline ester compound, and thus forming a reaction product comprising a quaternized imidazoline ester compound and, optionally, an imidazoline ester compound, involves the following steps.

In the quaternization process of the present invention, an anhydrous melt is initially formed containing an imidazoline ester compound of the formula

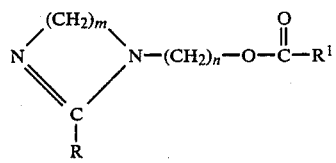

wherein R and R[1] are, independently, a $C_{11}$–$C_{21}$ hydrocarbyl group, preferably a $C_{13}$–$C_{17}$ alkyl group, and m and n are, independently, from 2 to 4, inclusive, preferably 2. The anhydrous melt is prepared at a temperature ranging from about 50° C. to about 100° C., preferably from about 70° C. to about 85° C.

The anhydrous melt containing the liquified imidazoline ester compound is then contacted, preferably in conjunction with agitation, with a quaternizing agent of the formula $R^2X$ or $R^2_2X$, wherein $R^2$ is a $C_1$–$C_3$ alkyl group, preferably methyl, or a benzyl group, and X is a halide, preferably chloride or bromide, or sulfate, to form a reaction mixture. The anhydrous melt is preferably contacted with from about 1 to 100 mole percent, more preferably from about 30 to about 90 mole percent, most preferably from about 40 to about 80 mole percent, of the quaternizing agent. The mole percentage of quaternizing agent is relative to the moles of imidazoline ester compound originally present in the anhydrous melt. The amount of quaternizing agent to be contacted with the anhydrous melt depends upon the amount of quaternized imidazoline ester compound desired in the final product.

When the quaternizing agent is in the gaseous phase, greater than 100 mole percent (relative to the moles of liquified imidazoline ester present in the anhydrous melt) of quaternizing agent may be added to the reaction vessel. A percentage of this gaseous quaternizing agent will occupy the head space in the reaction vessel above the anhydrous melt and typically will not contact or participate in quaternization reactions with the liquified imidazoline ester compound.

Preferred quaternizing agents include methyl, ethyl and propyl halides, dimethyl or diethyl sulfate, benzyl chloride or benzyl bromide, with dimethyl and diethyl sulfate being preferred and methyl chloride being most preferred.

The method of contacting the quaternizing agent with the liquified imidazoline ester compound depends on the phase of the quaternizing agent. If the quaternizing agent is in a gaseous state at the quaternization temperature, as in the case with methyl chloride, then the quaternizing agent is preferably either bubbled through or charged into a reactor vessel under pressure with the anhydrous melt. If the quaternizing agent is a liquid at the quaternization temperature, then it is preferably added to the anhydrous melt via titration or other means.

The liquid reaction mixture containing the liquified imidazoline ester compound and quaternizing agent is maintained at a temperature ranging from about 50° C. to about 100° C., preferably from about 70° C. to about 85° C., for a period of time sufficient to react substantially all of the quaternizing agent with the imidazoline ester compound to form a quaternized imidazoline ester compound of the formula

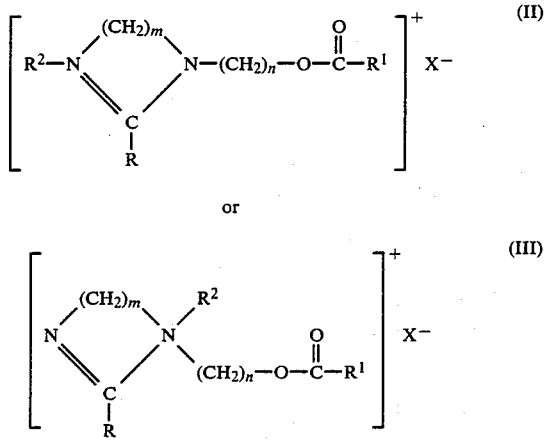

or mixtures thereof, wherein R, R$^1$, R$^2$, X$^-$, m and n are as hereinbefore defined. The time period the anhydrous melt is maintained within the prescribed quaternization reaction temperatures ranges from about 1 to about 4 hours. Any unreacted quaternizing agent will be removed from the reaction product through known processes, such as stripping.

Importantly, the quaternization reaction between the quaternizing agent and the imidazoline ester compound is carried out in the absence of lower alcohol solvents in order to avoid transesterification reactions between the imidazoline ester compound and the lower alcohol solvents. By carrying out the quaternization in the absence of lower alcohol solvents, improved product yield and purity can be obtained. The quaternization must also be carried out under anhydrous conditions to avoid hydrolysis of the imidazoline ester reactant.

The imidazoline ester compound which is quaternized may be formed using standard reaction chemistry methods. A preferred method is a two-step process for preparing a di-substituted imidazoline compound, as disclosed in pending U.S. patent application Ser. No. 07/287,922 filed Dec. 21, 1988, the disclosure of which is incorporated herein by reference. In the first process step of this reference, a mono-substituted imidazoline intermediate compound is prepared by reacting an acylating agent with a polyalkylene polyamine having two or three amino groups in a liquid reaction mixture. Preferably the reaction mixture is rendered in liquid form by heating the reactants above their melting point and then combining the reactants in their molten state. The acylating agents used in the first step may be selected from fatty acids, fatty acid halides, fatty acid anhydrides, or fatty acid short chain esters.

Optionally, but not preferably, the liquid reaction mixture of the first process step of this reference may also contain solvents which are compatible with the reactants in the liquid reaction mixture. However, any such solvents which comprise lower alcohol solvents must be removed from the liquid reaction mixture of the first process step by methods known in the art before quaternization of the final di-substituted imidazoline product.

In the second process step, the mono-substituted imidazoline intermediate formed in the first process step is further reacted in the same reaction mixture to substitute an ester-interrupted second long chain group onto the intermediate imidazoline compound. The second step may optionally be carried out in the presence of a esterification catalyst which is preferred.

The esterifying agents useful herein include short-chained monoesters, and fatty acids and various esters of polyhydric alcohols, such as fatty acid mono-, di- and triglycerides. In general, short-chained monoesters are the most preferred type of esterifying agent.

Under certain conditions, the imidazoline ester compound product prepared in this two-step process may optionally be quaternized directly, by the process of the present invention, in the same reaction vessel in which it is prepared.

FABRIC CONDITIONING COMPOSITIONS

Fabric conditioning compositions containing the reaction product prepared herein are especially suitable in the rinse cycle of a textile laundering operation. Liquid fabric conditioning compositions prepared using the reaction product of this invention are preferably aqueous and contain from about 1% by weight to about 30% by weight of the reaction product of this invention in a dispersion.

Since the components of the reaction product of the present invention contain ester groups, they are believed to be both biodegradable and labile to hydrolysis. Therefore, care should be taken in handling any fabric softening compositions containing such compounds. For example stable liquid compositions herein are preferably formulated at a pH in the range of about 1.5 to about 5.0, most preferably at a pH in the range of about 1.8 to about 3.5. The pH can be adjusted by Bronsted acid. Examples of suitable Bronsted acids include the inorganic mineral acids, carboxylic acids, in particular the low molecular weight (C$_1$-C$_5$) carboxylic acids, and alkylsulfonic acids. Suitable inorganic acids include HCl, H$_2$SO$_4$, HNO$_3$ and H$_3$PO$_4$. Suitable organic acids include formic, acetic, benzoic, methylsulfonic and ethylsulfonic acid. Preferred acids are hydrochloric and phosphoric acids.

Alternatively, solid fabric softening and antistatic compositions can be prepared from the reaction product of this invention. For example, the reaction product of this invention can be adsorbed on particulate solids such as potassium sulfate, micronized silica, powdered urea, and the like, and added to a laundry rinse bath. Alternately, such solid compositions can be releasably affixed to a solid carrier (e.g., paper towel, non-woven fabric, or the like) and tumbled with damp fabrics in a hot air clothes dryer in the manner of the BOUNCE ® brand dryer added product known in commercial practice. Generally, such solid compositions will contain from about 1% to about 20% by weight of the reaction product of this invention and from about 80% to about 99% by weight of the solid carrier.

Compositions containing the reaction product of this invention are also useful in hair conditioning applications. Such compositions typically comprise from about 0.1% by weight to about 20% by weight of the reaction product of this invention in a dispersion.

Quaternized Ester-ammonium Softening Compound

Fabric conditioning compositions containing the product of the instant invention may optionally contain other non-imidazoline ester fabric conditioning (softening/antistatic) agents. Such other agents may be described as cationic and nonionic organic materials which are generally employed as fabric conditioning agents during the rinsing cycle of the household laundering process. Quaternized ester ammonium softening compounds may be selected from the group consisting of

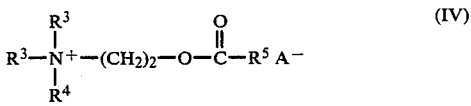

or

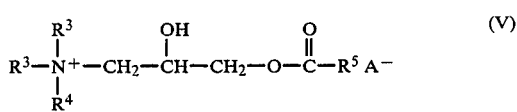

or

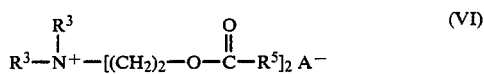

and mixtures thereof, wherein each $R^3$ substituent is a $C_1$–$C_6$, preferably a $C_1$–$C_3$, hydrocarbyl group, most preferably methyl; $R^4$ is a short chain hydrocarbyl group or a $C_{14}$–$C_{22}$ hydrocarbyl group, preferably a $C_{16}$–$C_{18}$ alkyl group, most preferably a straight chain $C_{18}$ alkyl group; $R^5$ is a long chain $C_{13}$–$C_{21}$ hydrocarbyl group, preferably a $C_{13}$–$C_{17}$ alkyl group, most preferably a $C_{17}$ straight chain alkyl group. The counterion $A^-$ is not critical herein, and can be any softener compatible anion. The preferred compounds can be considered to be monoester variations of ditallow dimethyl ammonium salts (e.g., DTDMAC, a widely used fabric softening compound).

As illustrative, nonlimiting examples there can be mentioned the following quaternized monoester amines (wherein all long chain alkyl substituents are straight chained):

$[CH_3]_2[C_{18}H_{37}]^+NCH_2CH_2OC(O)C_{15}H_{31}Br^-$
$[CH_3]_2[C_{18}H_{37}]^+NCH_2CH_2OC(O)C_{17}H_{35}Br^-$
$[CH_3]_2[C_{16}H_{33}]^+NCH_2CH_2OC(O)C_{17}H_{35}Cl^-$
$[C_2H_5]_2[C_{17}H_{35}]^+NCH_2CH_2OC(O)C_{13}H_{27}Cl^-$
$[C_2H_5][CH_3][C_{18}H_{37}]^+NCH_2CH_2OC(O)C_{14}H_{29}CH_3SO_4^-$
$[C_3H_7][C_2H_5][C_{16}H_{33}]^+NCH_2CH_2OC(O)C_{15}H_{31}Cl^-$
$(iso\text{-}C_3H_7)[CH_3][C_{18}H_{37}]^+NCH_2CH_2OC(O)C_{15}H_{31}I^-$ Illustrative, nonlimiting examples of useful quaternized two hydroxypropyl monoester ammonium salts (wherein long chain alkyl substituents are straight chain) include:

$[CH_3]_2[C_{18}H_{37}]^+NCH_2CH(OH)CH_2OC(O)C_{17}H_{35}Br^-$
$[CH_3]_2[C_{16}H_{33}]^+NCH_2CH(OH)CH_2OC(O)C_{15}H_{31}Cl^-$
$[C_2H_5]_2[C_{17}H_{35}]^+NCH_2CH(OH)CH_2OC(O)C_{15}H_{31}Cl^-$
$[C_2H_5][CH_3][C_{18}H_{37}]^+NCH_2CH(OH)CH_2OC(O)C_{17}H_{35}CH_3SO_4^-$
$[C_3H_7][C_2H_5][C_{16}H_{33}]^+NCH_2CH(OH)CH_2OC(O)C_{15}H_{31}Cl^-$
$(iso\text{-}C_3H_7)[CH_3][C_{18}H_{37}]^+NCH_2CH(OH)CH_2OC(O)C_{15}H_{31}I^-$ As with the components of the reaction product of the present invention, the foregoing compounds are somewhat labile to hydrolysis and should be handled in the same manner as described hereinbefore, i.e., the pH of the fabric softening composition should be in the range of from about 1.5 to 5.0, preferably from 1.8 to 3.5.

Liquid Carrier

The aqueous compositions containing the product of the present invention also comprise a liquid carrier, e.g. water, which may optionally contain a $C_1$–$C_4$ monohydric alcohol. However, it is critical that if the compositions are to contain such monohydric alcohol solvents, the alcohols must be added after quaternization is completed in order to minimize any potential transesterification reaction with the imidazoline ester compound.

The softening compounds prepared in this invention are insoluble in such water-based carriers and, thus, are present as a dispersion of fine particles therein. Such particles are preferably submicron in size, more preferably having an average diameter of from about 0.18 to about 0.50 micron, and are conventionally prepared by high shear mixing which disperses the compounds into fine particles. A method of preparation of a preferred dispersion is disclosed in detail in examples following hereinafter. Again, since the softening compounds are hydrolytically labile, care should be taken to avoid the presence of base and to keep the processing temperature and pH in the ranges specified herein.

The particle dispersions of the foregoing type can optionally be stabilized against settling by means of standard nonbase emulsifiers, especially nonionic extenders. Such nonionics and their usage levels, have been disclosed in U.S. Pat. No. 4,454,049, McGilp et al, issued June 12, 1984, the disclosure of which is incorporated herein by reference. Specific examples of nonionic extenders suitable for use in the compositions herein include glycerol esters (preferably glycerol monostearate), fatty alcohols, ethoxylated linear alcohols, and mixtures thereof. The nonionic, if used, is typically used at a level from about 0.1% to about 10% by weight of the composition.

Conventional quaternary ammonium softening agents

Compositions containing the product of the present invention may further comprise a conventional mono- or di(higher alkyl) quaternary ammonium softening agent. The compositions herein can contain from 0% to about 25% (preferably from about 0.1% to about 10%) of the conventional di(higher alkyl)quaternary ammonium softening agent.

"Higher alkyl", as used in the context of the conventional quaternary ammonium salts herein, means alkyl groups having from about 8 to about 30 carbon atoms, preferably from about 11 to about 22 carbon atoms. Examples of such conventional quaternary ammonium salts include:
(i) acyclic quaternary ammonium salts having the formula:

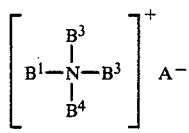

wherein $B^1$ is an acyclic aliphatic $C_{14}$–$C_{22}$ hydrocarbyl group, $B^3$ is a $C_1$–$C_4$ saturated alkyl or hydroxyalkyl group, $B^4$ is selected from $(CH_2)_2OH$, $B^1$ and $B^3$, and A is an anion;

(ii) quaternary ammonium salts having the formula:

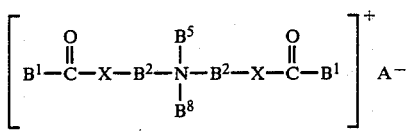

wherein $B^1$ is an acyclic aliphatic $C_{15}$–$C_{22}$ hydrocarbon group, $B^2$ is a divalent alkylene group having 1 to 3 carbon atoms, $B^5$ and $B^8$ are $C_1$–$C_4$ saturated alkyl or hydroxyalkyl groups, X is NH or O, preferably O, and A is an anion;

(iii) alkoxylated quaternary ammonium salts having the formula:

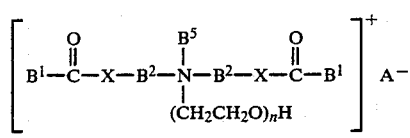

wherein n is equal to from about 1 to about 5, and $B^1$, $B^2$, $B^5$, X and A are as defined above;

(iv) substituted imidazolinium salts having the formula:

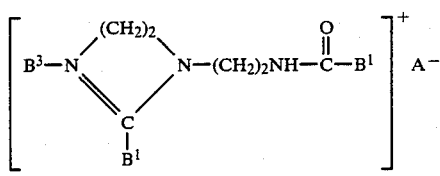

wherein $B^1$, $B^3$ and A are as defined above.

Examples of component (i) are the well known mono- and di-alkyl, di- and tri-methyl ammonium salts such as mono(hydrogenated tallow) trimethyl ammonium chloride (MTTMAC), monotallow trimethyl ammonium methylsulfate, ditallow dimethyl ammonium chloride, ditallow dimethyl ammonium methylsulfate, di(hydrogenated tallow) dimethyl ammonium chloride, dibehenyl dimethyl ammonium chloride, and tallow dimethyl (2-hydroxyethyl) ammonium chloride.

Examples of components (ii) and (iii) are methylbis(-tallowamidoethyl) (2-hydroxyethyl) ammonium methylsulfate and methylbis (hydrogenated tallowamidoethyl) (2-hydroxyethyl) ammonium methylsulfate, wherein $B^1$ is an acyclic aliphatic $C_{15}$–$C_{17}$ hydrocarbon group, $B^2$ is an ethylene group, $B^5$ is a methyl group, $B^8$ is a hydroxyalkyl group and A is a methylsulfate anion; these materials are available from Sherex Chemical Company Inc., located in Dublin, Ohio, under the trade names Varisoft ® 222 and Varisoft ® 110, respectively.

Examples of component (iv) include methyl-1-hydrogenated tallow amido ethyl-2-hydrogenated tallow imidazolinium-methyl sulfate (Varisoft 445, marketed by Sherex Chemical Company, Inc.) and methyl-1-tallow amido ethyl-2-tallow imidazolinium methyl sulfate (Varisoft 475, marketed by Sherex Chemical Company, Inc.).

Preferred conventional quaternary ammonium softening agents include MTTMAC and tallow dimethyl (2-hydroxyethyl) ammonium chloride. The MTTMAC compound is especially preferred when used in rinse-added fabric softening compositions which are added to the rinse cycle following washings in detergents such as ALL ®, TIDE ® and WISK ®. A preferred concentration of MTTMAC ranges from about 0.1% to about 3.0% by weight, with the most preferred concentration ranging from about 0.3% to about 1.0% by weight.

Imidazoline Softeninq Agents

Compositions containing the reaction product of the present invention may further comprise substituted imidazoline compounds having the formula:

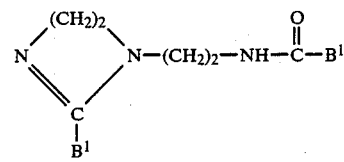

wherein $B^1$ is as already defined herein.

Examples of such imidazoline compounds include 1-hydrogenated tallow ethyl amido-2-hydrogenated tallow imidazoline (marketed by Sherex Chemical Company, Inc.) and 1-tallow ethyl amido-2-tallow imidazoline.

Free amines

The liquid compositions herein should be substantially free (generally less than about 1%) of free (i.e., unprotonated) acyclic amines.

Minor amounts of protonated amines, typically from about 0.05% to about 1.0%, namely primary, secondary and tertiary amines having, at least, one straight-chain organic group of from about 12 to about 22 carbon atoms may be used in the compositions of the present invention as emulsifiers to enhance dispersion stability. Examples of amines of this class are ethoxyamines, such as monotallow dipolyethoxyamine, having a total of from about 2 to about 30 ethoxy groups per molecule. Other such amines include diamines such as tallow-N,N,N-tris(2-hydroxyethyl)-1,3-propylenediamine (Jet Amine DT-3, marketed by Jetco Chemicals, Inc., located in Corsicana, Tex.), or $C_{16}$–$C_{18}$-alkyl-N-bis(2-hydroxyethyl)amines (e.g., Jet Amine PHT-2, marketed by Jetco Chemicals, Inc). Examples of the above compounds are those marketed under the trade names GENAMIN C, S, O and T, by American Hoechst Corporation, located in Sommerset, N.J.

It is preferred that emulsifiers selected from such amines not be included in any compositions prepared using the product of this invention. If such amines are included, care must be taken to ensure that amines are protonated with acid during formulation in order to minimize hydrolysis caused by the amines to the compounds comprising the reaction product of this invention.

Silicone Component

The present compositions may contain silicones to provide additional benefits such as ease of ironing and improved fabric feel. The preferred silicones are polydimethylsiloxanes of viscosity of from about 100 centistokes (cs) to about 100,000 cs, preferably from about 200 cs to about 60,000 cs. These silicones can be used as is, or can be conveniently added to the softener compositions in a preemulsified form which is obtainable directly from the suppliers. Examples of these preemulsified silicones are a 60% emulsion of polydimethylsiloxane (350 cs) sold by Dow Corning Corporation, located in Midland, Mich., under the trade name DOW CORNING ® 1157 Fluid and a 50% emulsion of polydimethylsiloxane (10,000 cs) sold by General Electric Company, located in Waterford, New York, under the trade name General Electric ® SM 2140 Silicone, and Silicone DC 1520, sold by Dow Corning Corporation. The optional silicone component can be used in an amount of from about 0.1% to about 6.0% by weight of the composition.

Thickening Agent

Optionally, the compositions herein contain from about 0.01% to about 3%, preferably from about 0.01% to about 2%, of a thickening agent. Examples of suitable thickening agents include: cellulose derivatives, synthetic high molecular weight polymers (e.g., carboxyvinyl polymer and polyvinyl alcohol), and cationic guar gums.

The cellulosic derivatives that are functional as thickening agents herein may be characterized as certain hydroxyethers of cellulose, such as Methocel ®, marketed by Dow Chemical U.S.A. The Dow Chemical Company, located in Midland, Mich., and certain cationic cellulose ether derivatives, such as Polymer JR-125 ®, JR-400 ®, and JR-30M ®, marketed by Union Carbide Corporation, located in Sommerset, N.J.

Other effective thickening agents are cationic guar gums, such as Gendrive ® 458, marketed by General Mills, Inc., located in Minneapolis, Minn.

Preferred thickening agents herein are selected from the group consisting of methyl cellulose, hydroxypropyl methylcellulose, hydroxybutyl methylcellulose, or mixtures thereof, said cellulosic polymer having a viscosity in 2% aqueous solution at 20° C. of from about 15 to about 75,000 centipoise.

Soil Release Agent

Optionally, the compositions herein contain from about 0.1% to about 10%, preferably from about 0.2% to about 5%, of a soil release agent. Preferably, such a soil release agent is a polymer. Polymeric soil release agents useful in the present invention include copolymeric blocks of terephthalate and polyethylene oxide or polypropylene oxide, and the like.

A preferred soil release agent is a copolymer having blocks of terephthalate and polyethylene oxide. More specifically, these polymers are comprised of repeating units of ethylene terephthalate and polyethylene oxide terephthalate at a molar ratio of ethylene terephthalate units to polyethylene oxide terephthalate units of from about 25:75 to about 35:65, said polyethylene oxide terephthalate containing polyethylene oxide blocks having molecular weights of from about 300 to about 2000. The molecular weight of this polymeric soil release agent is in the range of from about 5,000 to about 55,000.

Another preferred polymeric soil release agent is a crystallizable polyester with repeat units of ethylene terephthalate units containing from about 10% to about 15% by weight of ethylene terephthalate units together with from about 10% to about 50% by weight of polyoxyethylene terephthalate units, derived from a polyoxyethylene glycol of average molecular weight of from about 300 to about 6,000, and the molar ratio of ethylene terephthalate units to polyoxyethylene terephthalate units in the crystallizable polymeric compound is between 2:1 and 6:1. Examples of this polymer include the commercially available materials Zelcon ® 4780 (from E. I. du Pont de Nemours & Company, located in Wilmington, Del.) and Milease ® T (from ICI Americas, Inc., located in Wilmington, Del.).

Highly preferred soil release agents are polymers of the generic formula:

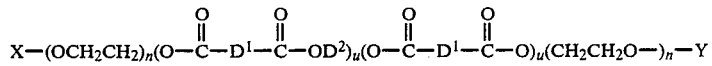

in which X can be any suitable capping group, with each Y being selected from the group consisting of H and alkyl or acyl groups containing from about 1 to about 4 carbon atoms, n is selected for water solubility and generally is from about 6 to about 113, preferably from about 20 to about 50, and u is critical to formulation in a liquid composition having a relatively high ionic strength. There should be very little material in which u is greater than 10. Furthermore, there should be at least 20%, preferably at least 40%, of material in which u ranges from about 3 to about 5.

The $D^1$ moieties are essentially 1,4-phenylene moieties. As used herein, the term "the $D^1$ moieties are essentially 1,4-phenylene moieties" refers to compounds where the $D^1$ moieties consist entirely of 1,4-phenylene moieties, or are partially substituted with other arylene or alkarylene moieties, alkylene moieties, alkylene moieties, or mixtures thereof Arylene and alkarylene moieties which can be partially substituted for 1,4-phenylene include 1,3-phenylene, 1,2-phenylene, 1,8-naphthylene, 1,4-naphthylene, 2,2-biphenylene, 4,4-biphenylene and mixtures thereof. Alkylene and alkenylene moieties which can be partially substituted include ethylene, 1,2-propylene, 1,4-butylene, 1,5-pentylene, 1,6-hexamethylene, 1,7-heptamethylene, 1,8-octamethylene, 1,4-cyclohexylene, and mixtures thereof.

For the $D^1$ moieties, the degree of partial substitution with moieties other than 1,4-phenylene should be such that the soil release properties of the compound are not adversely affected to any great extent. Generally, the degree of partial substitution which can be tolerated will depend upon the backbone length of the compound, i.e., longer backbones can have greater partial substitution for 1,4-phenylene moieties. Usually, compounds where the $D^1$ comprise from about 50% to about 100% 1,4-phenylene moieties (from 0 to about 50% moieties other than 1,4-phenylene) have adequate soil release activity. For example, polyesters made according to the present invention with a 40:60 mole ratio of isophthalic (1,3-phenylene) to terephthalic (1,4-phenylene) acid have adequate soil release activity. However, because most polyesters used in fiber making comprise ethylene terephthalate units, it is usually desirable to minimize the degree of partial substitution with moieties other than 1,4-phenylene for best soil release activity. Preferably, the $D^1$ moieties consist entirely of (i.e., comprise 100%) 1,4-phenylene moieties, i.e., each $D^1$ moiety is 1,4-phenylene.

For the $D^2$ moieties, suitable ethylene or substituted ethylene moieties include ethylene, 1,2-propylene, 1,2-butylene, 1,2-hexylene, 3-methoxy-1,2-propylene and mixtures thereof. Preferably, the $D^2$ moieties are essentially ethylene moieties, 1,2-propylene moieties or mixtures thereof. Inclusion of a greater percentage of ethylene moieties tends to improve the soil release activity of compounds. Surprisingly, inclusion of a greater percentage of 1,2-propylene moieties tends to improve the water solubility of the compounds.

Therefore, the use of 1,2-propylene moieties or a similar branched equivalent is desirable for incorporation of any substantial part of the soil release component in the liquid fabric softener compositions. Preferably, from about 75% to about 100%, more preferably from about 90% to about 100%, the $D^2$ moieties are 1,2-propylene moieties.

The value for each n is at least about 6, and preferably is at least about 10. The value for each n usually ranges from about 12 to about 113. Typically, the value for each n is in the range of from about 12 to about 43.

A more complete disclosure of these highly preferred soil release agents is contained in European Patent Application 185,427, Gosselink, published June 25, 1986, the disclosure of which is incorporated herein by reference.

Viscosity Control Agents

Viscosity control agents can be used in the compositions of the present invention (preferably in concentrated compositions). Examples of organic viscosity modifiers are fatty acids and esters, fatty alcohols, and water-miscible solvents such as short chain alcohols. Examples of inorganic viscosity control agents are water-soluble ionizable salts. A wide variety of ionizable salts can be used. Examples of suitable salts include sodium citrate and the halides of the group IA and IIA metals of the Periodic Table of the Elements, e.g., calcium chloride, magnesium chloride, sodium chloride, potassium bromide and lithium chloride. Calcium chloride is preferred. The ionizable salts are particularly useful during the process of mixing the ingredients to make the compositions herein, and later to obtain the desired viscosity. The amount of ionizable salts used depends on the amount of active ingredients used in the compositions and can be adjusted according to the desires of the formulator. Typical levels of salts used to control the composition viscosity are from about 20 to about 3,000 parts per million (ppm), preferably from about 20 to about 2,000 ppm, by weight of the composition.

In addition to their role as viscosity agents, the ionizable salts mentioned above also function as electrolytes and can further improve the stability of the compositions herein. A highly preferred electrolyte is calcium chloride. Typical levels of use of the electrolyte are from about 20 to about 3,000 parts per million (ppm), preferably from about 20 to about 2,000 ppm by weight of the compositions.

Bactericides

Examples of bactericides used in the compositions of this invention include glutaraldehyde, formaldehyde, 2-bromo-2-nitro-propane-1,3-diol sold by Inolex Chemicals, located in Philadelphia, Pa., under the trade name Bronopol ®, and a mixture of 5-chloro-2-methyl-4-isothiazoline-3-one and 2-methyl-4-isothiazoline-3-one sold by the Rohm and Haas Company, located in Philadelphia, Pa., under the trade name Kathon ® CG/ICP. Typical levels of bactericides used in the present compositions are from about 1 to about 1,000 ppm by weight of the composition.

Other Optional Ingredients

The present invention can include other optional components conventionally used in textile treatment compositions, for example, colorants, perfumes, preservatives, optical brighteners, opacifiers, fabric conditioning agents, surfactants, stabilizers such as guar gum and polyethylene glycol, anti-shrinkage agents, anti-wrinkle agents, fabric crisping agents, spotting agents, germicides, fungicides, anti-oxidants such as butylated hydroxy toluene, anti-corrosion agents, clays (when a solid composition is releasably affixed to a solid carrier) and the like.

In the method aspect of this invention, fabrics or fibers (including hair) are contacted with an effective amount, generally from about 20 ml to about 300 ml (per 2.5 kg of fiber or fabric being treated), of the compositions herein in an aqueous bath. Of course, the amount used is based upon the judgment of the user, depending on concentration of the composition, fiber or fabric type, degree of softness desired, and the like. Typically, about 50–100 ml. of an 8% dispersion of the softening compounds is used in a 83 l laundry rinse bath to soften and provide antistatic benefits to a 2.5 kg load of mixed fabrics. Preferably, the rinse bath contains from about 48 ppm to about 96 ppm of the fabric softening compositions herein.

The following examples illustrate the practice of the present invention but are not intended to be limiting thereof.

EXAMPLE I

A reaction product containing a quaternized imidazoline ester compound is prepared as follows:

Place 10.0 g of imidazoline ester compound of the formula

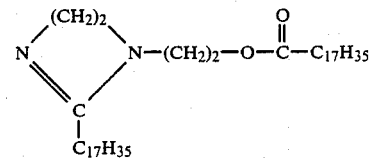

into a glass autoclave sleeve and then purge the autoclave with argon gas to remove any air and moisture. Melt the imidazoline ester compound by heating it to 80° C. With the autoclave pressure at 0 kilograms per square centimeter gauge (kscg), introduce gaseous methyl chloride from a gas cylinder into the autoclave at cylinder pressure (approximately 5.8 kscg). Maintain the temperature of the contents of the autoclave at approximately 80° C. for 2 hours while agitating the autoclave contents. After 2 hours, purge the autoclave with argon gas to remove residual methyl chloride gas. The resulting product mixture will contain a high yield of quaternized imidazoline ester compound of the formula

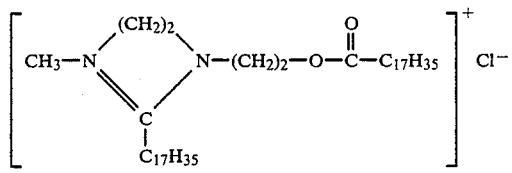

EXAMPLE II

A reaction product containing a quaternized imidazoline ester compound is prepared as follows:

Place 2.0 g of imidazoline ester compound of the formula

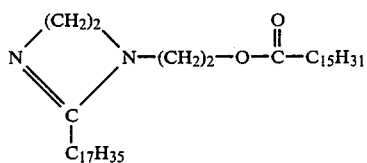

and a magnetic stir bar into a small glass seal-tube reaction vessel. Add 0.5 g of methyl iodide to the tube by syringe. Hermetically seal the tube and heat its contents to 80° C. Maintain the temperature of the tube contents at 80° C. for 4 hours while stirring. After 4 hours open the sealed tube and allow any methyl iodide residue to evaporate. The resulting product mixture will contain a high yield of quaternized imidazoline ester compound of the formula

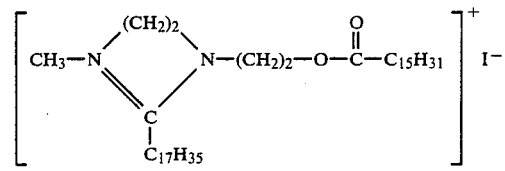

EXAMPLE III

A reaction product containing a quaternized imidazoline ester compound is prepared as follows:

Place 2.0 g of imidazoline ester compound of the formula

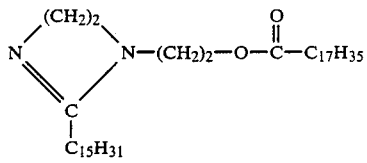

and a magnetic stir bar into a 10 ml round bottomed flask. Add 0.4 g of dimethyl sulfate to the flask. Stopper the flask tightly and heat its contents to 80° C. Maintain the temperature of the flask contents at 80° C. for 4 hours while stirring. The resulting product mixture will contain a high yield of quaternized imidazoline ester compound of the formula

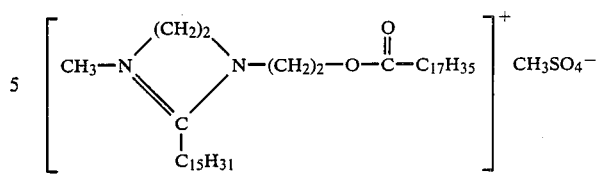

EXAMPLE IV

A reaction product containing a quaternized imidazoline ester compound is prepared as follows:

Place 1.82 g of imidazoline ester compound of the formula

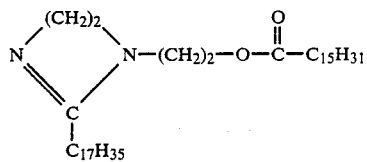

and a magnetic stir bar into a small glass seal-tube reaction vessel. Add 0.285 g of methyl bromide to the tube by syringe. Hermetically seal the tube and heat its contents to 80° C. Maintain the temperature of the tube contents at 80° C. for 4 hours while stirring. After 4 hours open the sealed tube and allow any methyl bromide residue to evaporate. The resulting product mixture will contain a high yield of quaternized imidazoline ester compound of the formula

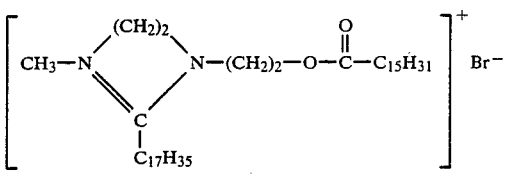

EXAMPLE V

A reaction product containing a quaternized imidazoline ester compound and an imidazoline ester compound is prepared as follows:

Place 90.0 kg of imidazoline ester compound of the formula

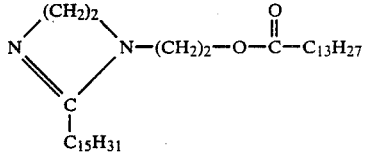

into a glass lined Pfaudler reactor, or other suitable corrosion resistant reactor. Heat the reactor contents to 70° C. and purge with $N_2$ gas to remove air and moisture. With the reactor at 0 kilograms per square centimeter gauge (kscg) introduce 5.0 kg of methyl chloride gas into the reactor at a pressure of 1.46 kscg. Maintain the temperature of the reactor at about 70° C. while agitating. After 2 hours, purge the reactor with $N_2$ gas to remove any unreacted methyl chloride. The resulting product mixture will contain about 60 mole percent of quaternized imidazoline ester compound of the formula

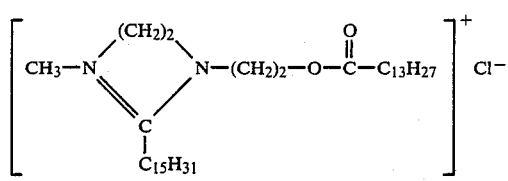

and about 40 mole percent of the initial imidazoline ester reactant.

EXAMPLE VI

A reaction product containing a quaternized imidazoline ester compound and an imidazoline ester compound is prepared as follows:

Place 90.9 kg of imidazoline ester compound of the formula

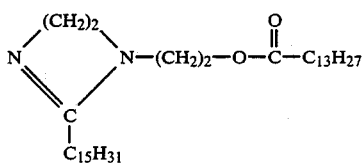

into a glass lined Pfaudler reactor, or other suitable corrosion resistant reactor. Heat the reactor contents to 80° C. and purge with N₂ gas to remove air and moisture. With the reactor at 0 kilograms per square centimeter gauge (kscg), introduce 16.7 kg of dimethyl sulfate into the reactor. Maintain the temperature of the reactor contents in the range of from 80° C. to 85° C. while agitating. The resulting product mixture will contain about 90 mole percent of quaternized imidazoline ester compound of the formula and about 10 mole percent of the initial imidazoline ester reactant.

EXAMPLE VII

A reaction product containing a quaternized imidazoline ester compound and an imidazoline ester compound is prepared as follows:

Place 600 g of imidazoline ester compound of the formula

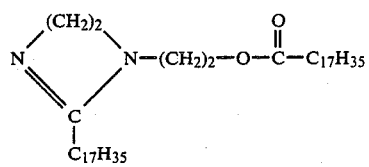

into a 2 liter round bottomed flask equipped with a N₂ gas inlet and outlet and overhead stirrer. Add 75 g of diethyl sulfate to the flask. Stopper the flask tightly and heat its contents to 750° C. Maintain the temperature of the flask contents at 75° C. while stirring. The resulting product mixture will contain about 47 mole percent of quaternized imidazoline ester compound of the formula

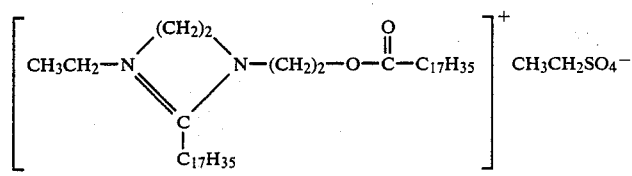

and about 53 mole percent of the initial imidazoline ester reactant.

EXAMPLE VIII

A storage-stable, liquid fabric-softening composition prepared using the reaction product of the present invention is comprised as follows:

| Ingredient | Percent (wt.) |
|---|---|
| [CH₃—N...N—(CH₂)₂—O—C(=O)—C₁₃H₂₇ / C₁₅H₃₁]⁺ Cl⁻ | 4.8% |
| N...N—(CH₂)₂—O—C(=O)—C₁₃H₂₇ / C₁₅H₃₁ | 3.2% |
| HCl | 0.2% |

| Ingredient | Percent (wt.) |
| --- | --- |
| Dye | 20 ppm |
| Water | Balance |

This composition is prepared as follows: place 0.80 kg of an imidazoline ester compound of the formula

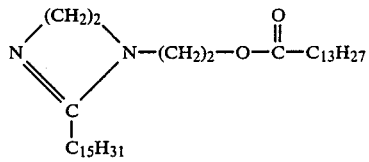

into a glass lined Pfaudler reactor, or other suitable corrosion resistant reactor. Heat the reactor contents to 80° C. and purge with $N_2$ gas to remove air and moisture. With the reactor at 0 kilograms per square centimeter gauge (kscg), introduce 0.044 kg of methyl chloride gas into the reactor at a pressure of 1.46 kscg. Maintain the temperature of the reactor contents in the range of from 80° C. to 85° C. while agitating. After 1 hour, purge the reactor with $N_2$ gas to remove any unreacted methyl chloride. The resulting product mixture will contain about 58 mole percent of quaternized imidazoline ester compound of the formula $$\left[ CH_3-N \underset{C}{\overset{(CH_2)_2}{\diagup \diagdown}} N-(CH_2)_2-O-\overset{O}{\underset{\|}{C}}-C_{13}H_{27} \right]^+ Cl^-$$
$$\underset{C_{15}H_{31}}{|}$$

and about 42 mole percent of the initial imidazoline ester reactant.

This product mixture is then heated to a temperature of about 80° C. to form a fluidized homogeneous "melt". The melt is then poured into 9.1 kg of hot (70° C.) water containing 20 ppm dye while maintaining continuous stirring with a low shear mixer. The pH of the water seat is adjusted to about 2.8 prior to the addition of the melt using 1N HCl. Midway through the addition of the melt to the water seat, half of the remaining HCl is added to the water seat and melt mixture. The resulting mixture is stirred an additional 5 minutes using a low-shear propeller blade mixer. The remaining HCl is added to the mixture after 4 minutes of stirring, thus adjusting the mixture pH to about 2.8. The mixture is sheared at 7,000 rpm for about 1 minute using a high-shear mixer (manufactured by the Tekmar Company, located in Cincinnati, Ohio). The softener actives of the resulting mixture have a typical particle size of about 0.2 micron and are dispersed in an aqueous dispersion. The aqueous dispersion has a viscosity of about 30 centipoise (@25° C.).

EXAMPLE IX

A storage-stable, liquid fabric-softening composition prepared using the reaction product of the present invention is comprised as follows:

| Ingredient | Percent (wt.) |
| --- | --- |
| $\left[ CH_3-N \underset{\underset{C_{15}H_{31}}{|}}{\overset{(CH_2)_2}{\diagup \diagdown}} N-(CH_2)_2-O-\overset{O}{\underset{\|}{C}}-C_{13}H_{27} \right]^+ Cl^-$ | 5.0% |
| $N \underset{\underset{C_{15}H_{31}}{|}}{\overset{(CH_2)_2}{\diagup \diagdown}} N-(CH_2)_2-O-\overset{O}{\underset{\|}{C}}-C_{13}H_{27}$ | 5.0% |
| Monotallow trimethyl ammonium chloride (MTTMAC) | 0.6% |
| Dye | 20 ppm |
| Polydimethylsiloxane (PDMS) | 0.32% |
| Silicone DC 1520 | 0.01% |
| HCl | 0.3% |
| Water | Balance |

This composition is prepared as follows: place 25 kg of imidazoline ester compound of the formula

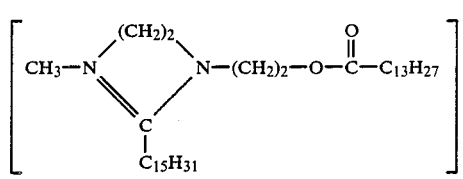

into a glass lined Pfaudler reactor, or other suitable corrosion resistant reactor. Heat the reactor contents to 80° C. and purge with $N_2$ gas to remove air and moisture. With the reactor at 0 kilograms per square centimeter gauge (kscg), introduce 1.2 kg of methyl chloride gas into the reactor at a pressure of 1.46 kscg. Maintain the temperature of the reactor contents in the range of from 80° C. to 85° C. while agitating. After 1.5 hours, purge the reactor with $N_2$ gas to remove any unreacted methyl chloride. The resulting product mixture will contain about 50 mole percent of quaternized imidazoline ester compound of the formula

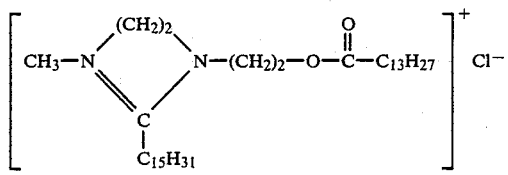

and about 50 mole percent of the initial imidazoline ester reactant.

One kilogram of the product mixture is heated to a temperature of about 70° C. to form a fluidized homogeneous "melt". The melt is then poured into 8.0 kg of hot (70° C.) water containing 20 ppm dye. The pH of the water seat is adjusted to about 2.8 prior to the addition of the melt using 1N HCl. Midway through the addition of the melt to the water seat, half the remaining 1N HCl is added to the water seat and melt mixture. 128.0 g of a 47% aqueous MTTMAC solution is added to the stirring mixture. This mixture is stirred an additional 5 minutes using a low-shear propeller blade mixer. The remaining 1N HCl is added to the mixture after about 4 minutes of stirring, thus bringing the mixture pH to about 2.8. The mixture is cooled to about 40° C. and 32.0 g of PDMS and 1.0 g of Silicone® DC 1520, marketed by Dow Corning Corporation, are added to the mixture with high-shear mixing (using a Tekmar mixer at 5000 rpm). The high-shear mixing is maintained for 2 minutes. The softener actives of the resulting mixture have a typical particle size of about 0.2 micron and are dispersed in an aqueous dispersion. The aqueous dispersion has a viscosity of about 30 centipoise (25° C.).

What is claimed is:

1. A process for quaternizing an imidazoline ester compound, said process comprising:

(a) forming an anhydrous melt of an imidazoline ester compound of the formula

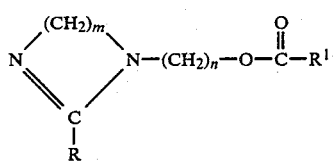 (I)

wherein R and $R^1$ are, independently, a $C_{11}$–$C_{21}$ hydrocarbyl group, and m and n are, independently, from 2 to 4 inclusive;

(b) contacting said anhydrous melt with a quaternizing agent of the formula $R^2X$ or $R^2_2X$, wherein $R^2$ is a $C_1$–$C_3$ alkyl or benzyl group and X is a halide or sulfate, to form a liquid reaction mixture, said liquid reaction mixture being maintained free of lower alcohol solvents; and (c) maintaining said liquid reaction mixture under anhydrous conditions at a temperature ranging from about 50° C. to about 100° C. for a period of time sufficient for substantially all of said quaternizing agent to react with said imidazoline ester compound to form a quaternized imidazoline ester compound of the formula

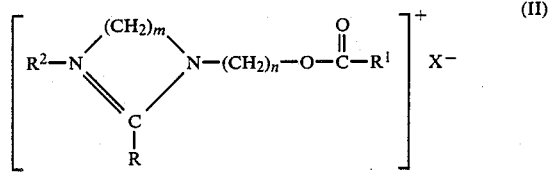 (II)

or

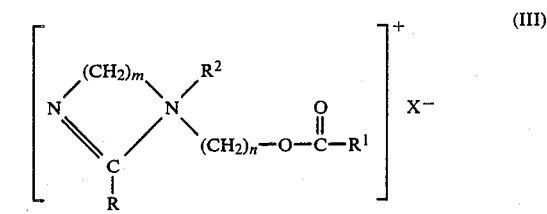 (III)

or mixtures thereof, wherein R, $R^1$, $R^2$, X, m and n are as defined in subparagraphs (a) and (b).

2. A process according to claim 1 wherein R and $R^1$ are, independently, a $C_{13}$–$C_{17}$ alkyl group, and m and n are each 2.

3. A process according to claim 2 wherein the quaternizing agent is a $C_1$–$C_3$ halide.

4. A process according to claim 3 wherein the quaternizing agent is methyl chloride.

5. A process according to claim 2 wherein the quaternizing agent is dimethyl sulfate.

6. A process according to claim 4 wherein said liquid reaction mixture is maintained at a temperature ranging from about 70° C. to about 85° C. to a period of from about 1 to about 4 hours.

7. A process for preparing a reaction product containing a quaternized imidazoline ester compound and, optionally, an imidazoline ester compound, said process comprising:

(a) forming an anhydrous melt of an imidazoline ester compound of the formula

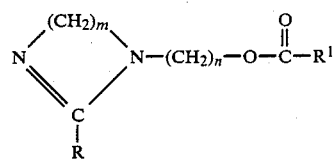

wherein R and $R^1$ are, independently, a $C_{11}$–$C_{21}$ hydrocarbyl group, and m and n are, independently, from 2 to 4 inclusive;

(b) contacting said anhydrous melt with a quaternizing agent of the formula $R^2X$ or $R^2_2X$, wherein $R^2$ is a $C_1$–$C_3$ alkyl or benzyl group and X is a halide or sulfate, to form a liquid reaction mixture, said liquid reaction mixture being maintained free of lower alcohol solvents; and (c) maintaining said liquid reaction mixture under anhydrous conditions at a temperature ranging from about 50° C. to about 100° C. for a period of time sufficient to form said reaction product, wherein said reaction product contains from about to 100 mole percent of a quaternized imidazoline ester compound of the formula

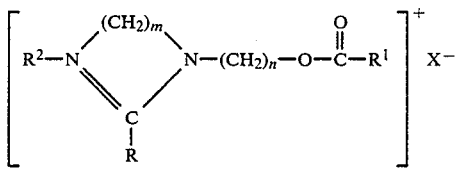

or

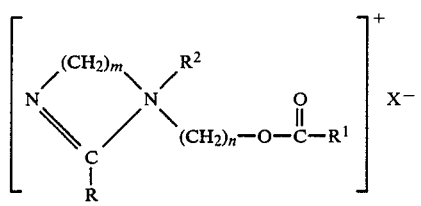 (III)

or mixtures thereof, wherein R, $R^1$, $R^2$, X, m and n are as defined in subparagraphs (a) and (b), and from 0 to about 99 mole percent of the imidazoline ester compound contained in subparagraph (a).

8. A process according to claim 7 wherein R and $R^1$ are, independently, a $C_{13}$-$C_{17}$ alkyl group, and m and n are each 2.

9. A process according to claim 8 wherein the quaternizing agent is a $C_1$-$C_3$ halide.

10. A process according to claim 9 wherein the quaternizing agent is methyl chloride.

11. A process according to claim 8 wherein the quaternizing agent is dimethyl sulfate.

12. A process according to claim 10 wherein said liquid reaction mixture is maintained at a temperature ranging from about 70 ° C. to about 85° C. to a period of from about 1 to about 4 hours.

13. A process according to claim 12 wherein from about 30 to about 90 mole percent of quaternizing agent is contacted with said anhydrous melt.

14. A process according to claim 13 wherein from about 40 to about 80 mole percent of quaternizing agent is contacted with said anhydrous melt.

15. A process according to claim 13 wherein the reaction product contains from about 30 to about 90 mole percent of quaternized imidazoline ester compound and from about 10 to about 70 mole percent of imidazoline ester compound.

16. A process according to claim 14 wherein the reaction product contains from about 40 to about 80 mole percent of quaternized imidazoline ester compound and from about 60 to about 20 mole percent of imidazoline ester compounds.

17. A process according to claim 16 wherein the imidazoline ester compound (a) is of the formula

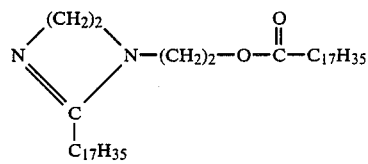

* * * * *

UNITED STATES PATENT AND TRADEMARK OFFICE
CERTIFICATE OF CORRECTION

PATENT NO. : 4,954,635

DATED : September 4, 1990

INVENTOR(S) : Theresa Rosario-Jansen and Glen D. Lichtenwalter

It is certified that error appears in the above-identified patent and that said Letters Patent is hereby corrected as shown below:

Column 10, line 53, "N,N,N -tris(2-hydroxyethyl)-1,3-propylenediamine" should be --N,N',N'-tris(2-hydroxyethyl)-1,3-propylenediamine--.

Column 18, line 31, "750°C." should be --75°C.--.

Signed and Sealed this

Third Day of March, 1992

*Attest:*

HARRY F. MANBECK, JR.

*Attesting Officer*      *Commissioner of Patents and Trademarks*